United States Patent [19]
Sincock

[11] Patent Number: 5,190,169
[45] Date of Patent: Mar. 2, 1993

[54] DEVICE AND METHOD FOR THE SAFE SECURING AND DISPOSAL OF SHARPS FROM MEDICAL TOOLS

[75] Inventor: Brian F. Sincock, Adelaide, Australia

[73] Assignee: Ausmedics Pty Ltd., Port Lincoln, Australia

[21] Appl. No.: 710,041

[22] Filed: Jun. 3, 1991

Related U.S. Application Data

[60] Continuation-in-part of Ser. No. 528,963, May 22, 1990, Pat. No. 5,047,019, which is a continuation-in-part of Ser. No. 265,707, Nov. 1, 1988, Pat. No. 4,973,315, and a continuation-in-part of Ser. No. 497,638, Mar. 23, 1990, and a continuation-in-part of Ser. No. 523,426, May 15, 1990, abandoned, which is a continuation-in-part of Ser. No. 265,707, Nov. 1, 1988, Pat. No. 4,973,315, and a continuation-in-part of Ser. No. 545,587, Jun. 29, 1990, Pat. No. 5,129,886, which is a division of Ser. No. 265,707, Nov. 1, 1988, Pat. No. 4,973,315.

[30] Foreign Application Priority Data

Nov. 4, 1987 [AU] Australia .................. PI5348
Oct. 26, 1989 [AU] Australia .................. PJ7069

[51] Int. Cl.5 .................................. A47F 7/00
[52] U.S. Cl. .................................. 211/60.1; 206/366; 604/192
[58] Field of Search .............. 211/60.1; 206/365, 366; 604/192, 110, 199

[56] References Cited

U.S. PATENT DOCUMENTS

| | | | |
|---|---|---|---|
| D. 271,239 | 11/1983 | Lemieux et al. | 604/192 X |
| 4,383,615 | 5/1983 | Aquino | 211/60.1 |
| 4,636,201 | 1/1987 | Ambrose et al. | 604/192 |
| 4,798,292 | 1/1989 | Hauze | 604/192 X |
| 4,890,734 | 1/1990 | Gach | 206/366 |
| 5,057,282 | 10/1991 | Linder | 206/366 X |
| 5,092,462 | 3/1992 | Sagstetter et al. | 604/192 X |

Primary Examiner—Robert W. Gibson, Jr.
Attorney, Agent, or Firm—Fish & Richardson

[57] ABSTRACT

An apparatus provides for the safe securing, removal and disposal of medical sharps. In a preferred embodiment, the apparatus comprises a holding tray with a plurality of apertures in a planar surface, with each aperture receiving and supporting a sheath for the disposal of medical sharps. Methods employing the apparatus are disclosed.

46 Claims, 9 Drawing Sheets

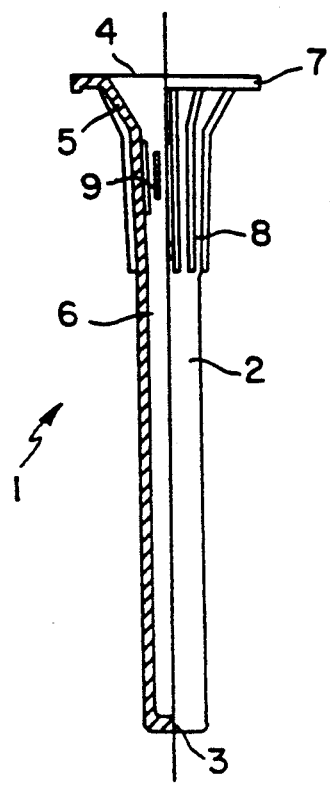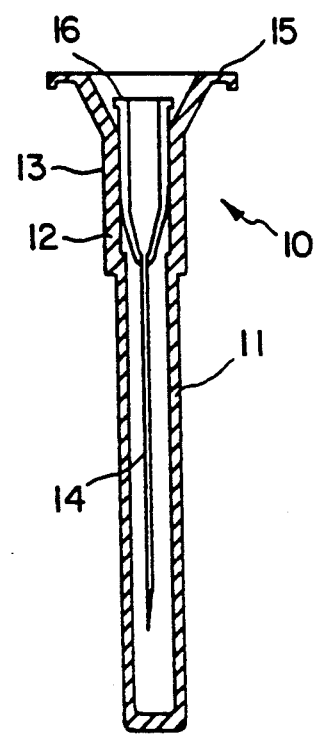
FIG. 1
FIG. 2
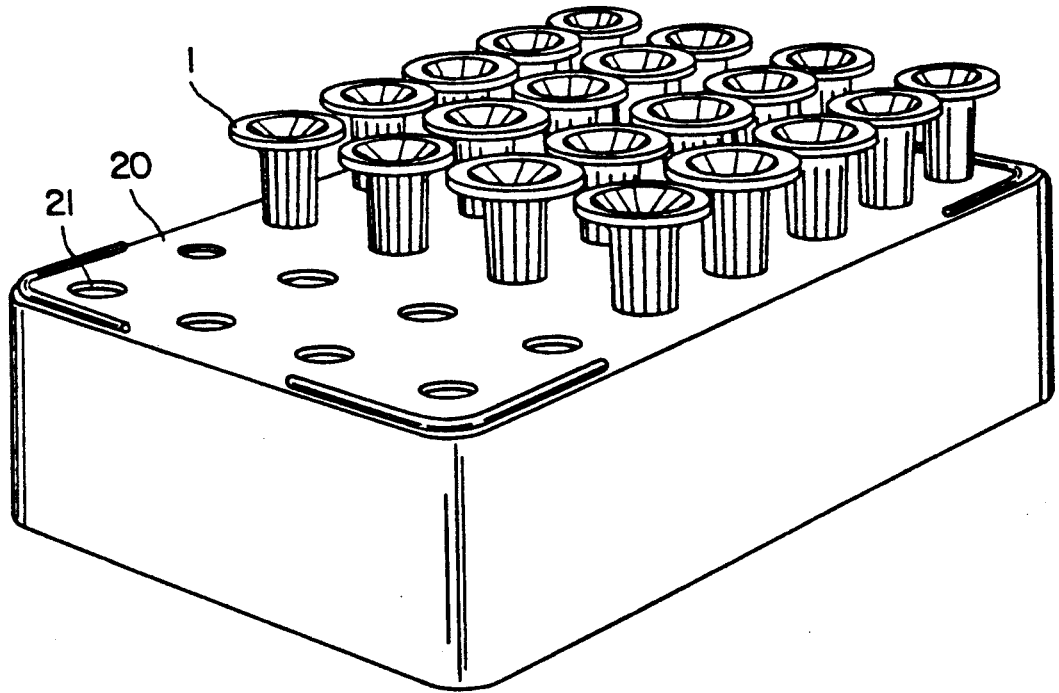
FIG. 3

DEVICE AND METHOD FOR THE SAFE SECURING AND DISPOSAL OF SHARPS FROM MEDICAL TOOLS

This application is a continuation-in-part of U.S. Ser. No. 07/528,963, filed May 22, 1990, now U.S. Pat. No. 5,047,019 which is a continuation-in-part of U.S. Ser. No. 07/265,707, filed Nov. 1, 1988, now U.S. Pat. No. 4,973,315, and U.S. Ser. No. 07/497,638, filed Mar. 23, 1990; a continuation-in-part of U.S. Ser. No. 07/523,426, filed May 15, 1990, now abandoned which is a continuation-in-part of U.S. Ser. No. 07/265,707, filed Nov. 1, 1988, now U.S. Pat. No. 4,973,315; and a continuation-in-part of U.S. Ser. No. 07/545,587, filed Jun. 29, 1990, which is a division of U.S. Ser. No. 07/265,707, filed Nov. 1, 1988, now U.S. Pat. No. 4,973,315.

This invention relates to improvements in the removal of sharp pointed sections of medical instruments and the safe disposal of such sharp sections.

Sharps may include needles for hypodermic syringes, canulas, scalpels, catheters or any other sharp pointed instruments used in medical treatment. Sharps are generally disposable and, because they have been used for treating ill people, may carry disease organisms or other infectious bodies.

In order to meet stringent health and safety regulations and to minimize transmission of bacteria, viruses, disease or other organisms having the potential to create disease or illness, the current practice is to dispose of either the sharp or needle section of a medical device, or the complete tool with the sharp or needle section attached, once the medical tool has been used and come into contact only once with a human body. In most cases, such as blood sample collection, it is necessary to remove the needle or other device from the medical tool and it is during this process that injuries may occur to medical personnel handling the medical tools. Such injuries are referred to as needle stick injuries, and the present invention relates to the prevention of needle stick injuries.

A further problem exists in the current procedure for the disposal of needles wherein the needles, either removed or unremoved from a syringe, are deposited into a storage container to be destroyed by burning or a similar procedure. However, needles may tend to puncture and project out of the sides of a container into which they have been placed and cause problems for disposal personnel as well as medical personnel who directly handle the medical tools. Hence, this invention is directed to preventing needles from being able to create such "downstream" injuries once they have been dropped into a disposal container.

It is one object of this invention, therefore, to alleviate the necessity to handle a needle or the boss of a needle during the removal or disposal process and to prevent that needle from being able to cause any further injury once removed or discarded.

In one form, this invention relates to a sheath for the disposal of medical sharps, the sheath comprising a tubular portion closed at one end and being open at the other, the open end of the sheath having a radially outwardly extending flange, the flange including means for guiding the tip of a medical sharp into the tube and the inner surface of the tube in the region of the flange including means for grippingly engaging a boss portion of the medical sharp.

Therefore, this sheath is long enough to completely encase the needle or sharp and rigidly hold it so that the needle or sharp cannot project out of the sides or the bottom of the sheath. Once the boss of the medical sharp is received and held in the gripping portion of the tube, the syringe or other device can be rotated to release the sharp from the medical tool and then one or both parts can be disposed of. Alternatively, the medical tool and the attached sharp may be disposed of as a single unit with the sharp safely secured within the sheath.

Preferably, the outer surface of the tube adjacent to the flange includes ribs to assist a user in manually grasping the sheath during the removal of a sharp from the remainder of the medical tool once the sharp is secured within the sheath. These ribs may also assist in preventing rotation of a sheath held within a holding tray.

The means for grippingly engaging the boss of a medical sharp may include a plurality of longitudinal ridges extending radially inward from the inner surface of the tube to enable gripping of the boss by the ridges.

Alternatively, the means for grippingly engaging the boss of the medical sharp may include an inside portion of the tube being substantially cylindrical and having a diameter to engage with an interference fit the boss of the medical sharp.

The means for guiding the tip of the medical sharp into the tube may comprise a bevelled surface between the flange and the inner surface of the tube.

Additionally, this invention relates to a sheath holding tray having an upper substantially planar horizontal surface with a plurality of apertures therein, the apertures receiving and supporting a plurality of sheaths as defined above with their open ends upward.

The sheath may be supported in the holding tray during the insertion of a sharp into a sheath by a user, wherein the user's second hand may be kept completely away from the tip of the medical sharp, thereby completely eliminating any danger of a needle-stick injury. After the boss of the medical sharp has been firmly engaged in the gripping portion of the tube, then the sheath, while still connected to the medical tool, may be removed from the tray and either disposed of as discussed above as a complete unit, with the sharp secured within the sheath, or the sheath with the sharp engaged therein can be safely removed from the medical tool and disposed of separately. If the holding tray includes means for preventing the rotation of a sheath held therein, then the medical sharp can be removed from the medical tool by a user with only one hand.

Alternatively, this invention relates to a medical sharp disposal tray having an upper substantially planar and horizontal surface with a plurality of tubes extending from apertures in the surface and having closed lower ends, each tube having a bevelled portion between the planar surface and the inner surface of the tube for assisting with guiding the tip of a medical sharp into the tube and means for grippingly engaging the boss at the base of a medical sharp when inserted into the tube. In this aspect of the invention, the medical sharps may be received in the tubes in the disposal tray, and when all of the tubes in the tray are filled with sharps, the entire lot may be disposed of.

It will be realized that where medical sharps have different arrangements of bosses or gripping means at the base of their pointed section then other gripping means are within the scope of this invention to enable the pointed section to be clearly protected as described above.

In the various forms of the invention, it is not necessary for a user to remove manually the needle section manually from the medical tool before it is inserted into the sheath or tube. Therefore, there is much less chance of injury from the medical sharp.

It may not be necessary for the user to remove the needle section from the medical tool prior to disposal and in this situation a firm downward movement of the sheath onto a hard surface, once it is installed onto the medical sharp, will more tightly affix the sheath to the needle section of the medical tool and the needle section to the medical tool itself so that the medical tool and sharp and sheath can be disposed of as a single unit. Again, this provides considerable safety because the needle cannot stick the user.

If desired, there may be further provided within each tube of either the sheath or the fixed construction as discussed above, a foam or other material to assist with holding a needle, particularly when the needles do not have a boss which can be easily engaged into the sheath.

In general, therefore, this invention provides a safe method for the removal of medical sharps from a medical tool and the safe disposal thereof. It will be particularly noted that the method requires only a one handed operation for the insertion of a sharp into a sheath, and therefore, as one hand is holding the medical tool the other hand can be placed well away so that there is no danger of a needle piercing the skin of a user and perhaps transmitting a disease such as AIDS. Additionally, in several embodiments the sharp can be removed form the remainder of the medical tool with only one hand.

This generally describes the invention but to more clearly assist with understanding the invention reference will now be made to the accompanying drawings which show preferred embodiments of the invention.

BRIEF DESCRIPTION OF THE DRAWINGS

FIG. 1 shows a partial cross-sectional view of a sheath for the removal and disposal of medical sharps.

FIG. 2 shows a cross-sectional view of an alternative sheath for the removal of medical sharps with a hypodermic syringe needle secured within the sheath.

FIG. 3 shows a first disposal tray with a number of sheaths supported therein.

DESCRIPTION OF THE PREFERRED EMBODIMENTS

Figure 4:
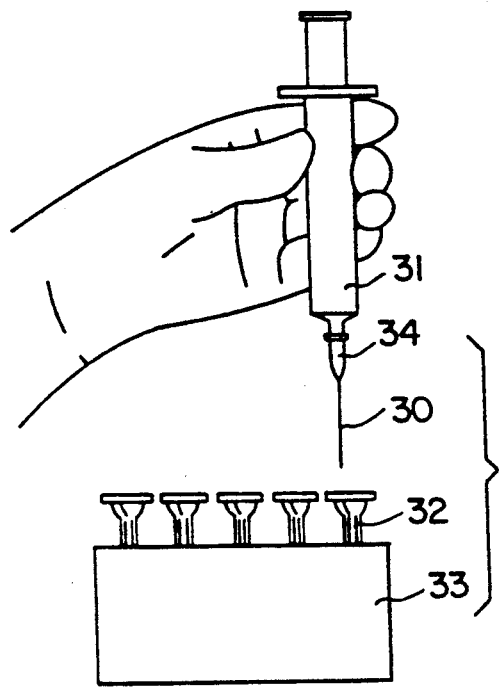
FIG. 4 to 8 show the various stages in the process of removal of a medical sharp from a hypodermic syringe.

The sheath 1 shown in FIG. 1 comprises a tubular portion 2 having a closed end 3 and an open end 4. The open end has a bevelled inner surface 5 to assist with guiding the tip of a medical sharp into the hollow part 6 of the tube 2. A flange 7 extends radially outwardly from the open end 4 of the sheath 1. On the outside of the sheath 1 are a number of ridges or ribs 8 underneath the flange 7 so that the outside of the sheath may be grasped while the needle is being removed from a syringe or other article of medical equipment once the boss has been engaged in the tube. The inner surface of the tube 2 immediately adjacent the open end includes longitudinal ridges 9 for grippingly engaging the boss of a medical sharp and assisting with the removal thereof.

An alternative embodiment of medical sharp sheath is shown in FIG. 2 with a hypodermic syringe needle engaged therein. In this embodiment, the gripping region 10 of the tube 11 includes a substantially cylindrical inner surface 12 for grippingly engaging with an interference fit the boss 13 of a medical sharp. The needle 14 of the medical sharp is well protected in the sheath and cannot move sideways and pierce the walls of the tubular portion of the sheath.

Additionally, it is noted that the top 16 of the boss is recessed well below the flange area 15, and therefore, the medical sharp cannot easily be removed for illegal further use.

FIG. 3 shows a number of sheaths 1 held in a tray 20. The tray includes a number of apertures 21 into which the sheaths 1 are received. The sheaths are supported in the tray but can easily be removed as they are loosely held by the ends of the ribs 8 on the edges of the apertures 21.

Now looking at FIGS. 4 to 8 which show the various stages in the removal of a needle, it can be seen in FIG. 4 that a syringe is being held in one hand with the point 30 of the syringe 31 pointed down into one of the sheaths 32 supported in the tray 33. It will be noted that only one hand is necessary to hold the syringe and the other hand is completely away from the tray 33.

Figure 5:
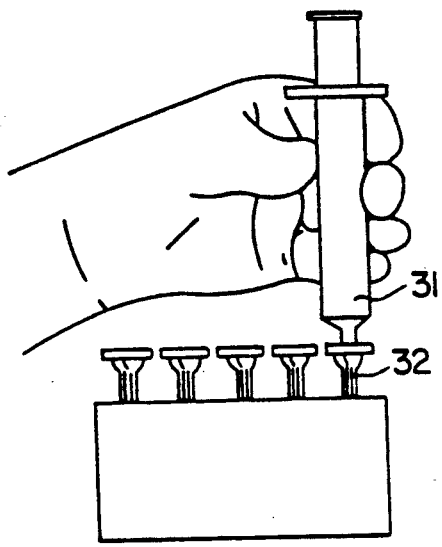
Figure 6:
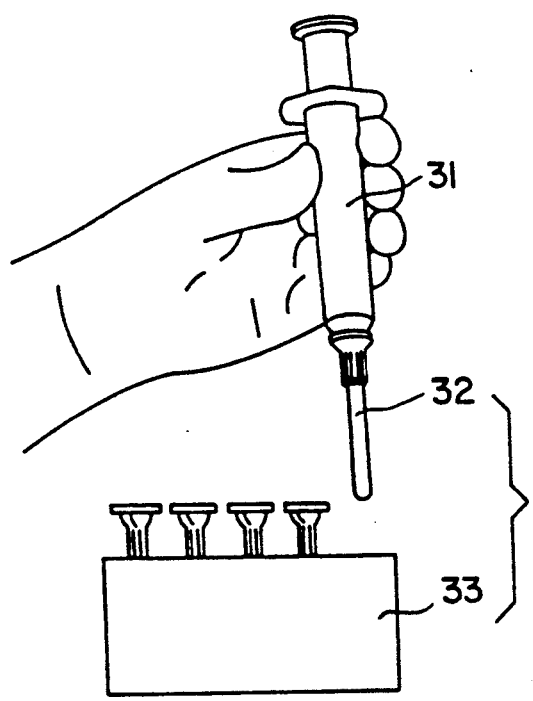
Figure 7:
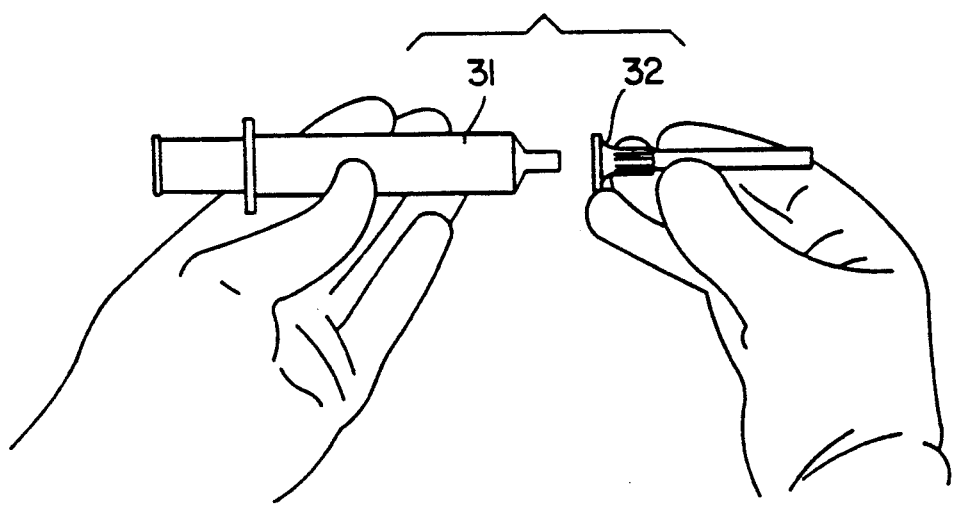

The needle 30 is pushed into the tube of the sheath 32 until the boss 34, as shown in FIG. 4, is completely pushed into the tube, as shown in FIG. 5. In FIG. 6, the sheath 32 is then engaged onto the syringe 31 and the sheath is removed from the tray 33. Then, as shown in FIG. 7, both hands can be used to remove the sheath 32 from the tool 31 leaving the needle fully protected by the sheath.

Figure 8:
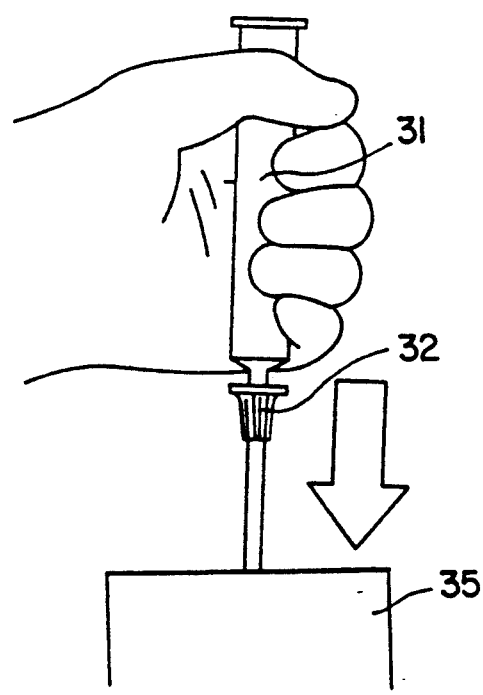

Alternatively, as shown in FIG. 8 from the stage shown in FIG. 6, the medical tool 31 with the sheath 32 engaged can be struck onto a hard surface 35, thereby firmly engaging the boss of the needle into the sheath and the syringe firmly into the boss. so that the two portions can be disposed of together with the needle secured in the sheath.

Figure 9:
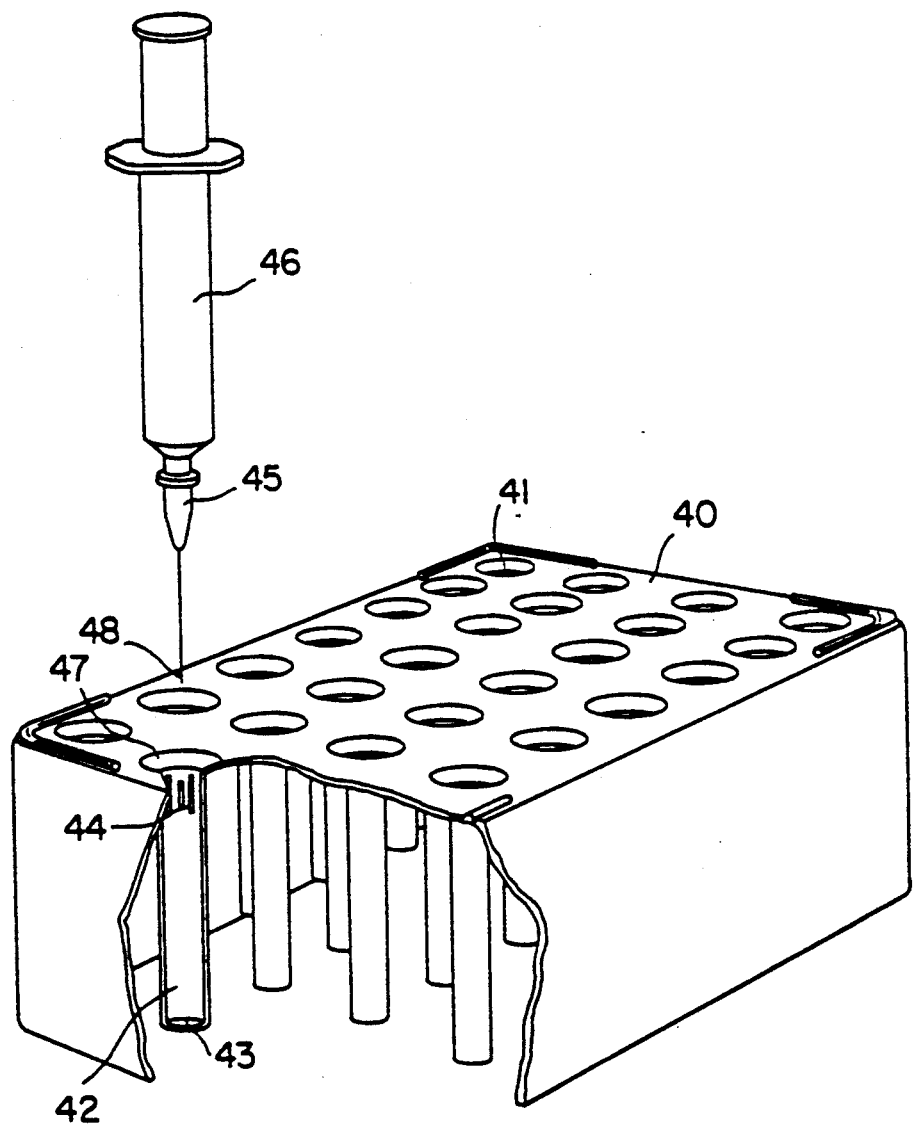
FIG. 9 shows a second embodiment of a medical sharp disposal tray.

FIG. 9 shows an alternative embodiment where a tray 40 includes a number of apertures 41. Each aperture includes a tubular portion 42 closed at its lower end 43 and including gripping ribs 44 to engage the boss 45 of a syringe 46. There is a bevelled portion 47 between the planar upper surface of the tray 40 and the tube 42 to assist with guiding the point 48 of a needle into the tube. Once the boss 45 has been firmly engaged in the tube 42, the syringe 46 then may be twisted to remove the needle therefrom and to leave the needle firmly engaged in the tray 40. After all of the apertures in the tray have been filled, the entire tray may be disposed of.

The materials of construction of the tray or molded sheath and tray combination shown in FIGS. 3 and 9, respectively, are preferably a plastic material, such as polyethylene or polypropylene. Alternatively, the tray may be made from cardboard, stainless steel or other suitable materials. Stainless steel and plastic offer the advantages of durability and easy clean-up, and stainless steel allows for sterilization of the materials. For plastic materials, the preferred method of construction is by injection-molding but other methods may be used.

The sheath may be manufactured from a plastic such as polyethylene or polypropylene by injection molding. A preferred material for the sheath is modified reinforced polypropylene, with talc-filled polypropylene being preferred. This material is sufficiently durable to prevent a needle from puncturing the sheath. Therefore, even if a needle is not inserted entirely vertically into a sheath by a user, the sheath is resistant to penetration by the point of the inserted needle.

FIGS. 10, 11, 12 and 13 show an alternative embodiment wherein a tray 50 includes a plurality of apertures 51. Each aperture 51 receives a sheath 1. The sheath 1 is provided with a flange 7, and the sheath 1 is supported by an aperture 51 such that either the outer edges of the flange 7 rests on a planar surface 55 of the tray 50, or the ribs 8 on an undersurface of a portion of the flange 7 rests on the planar surface 55.

Figure 11:
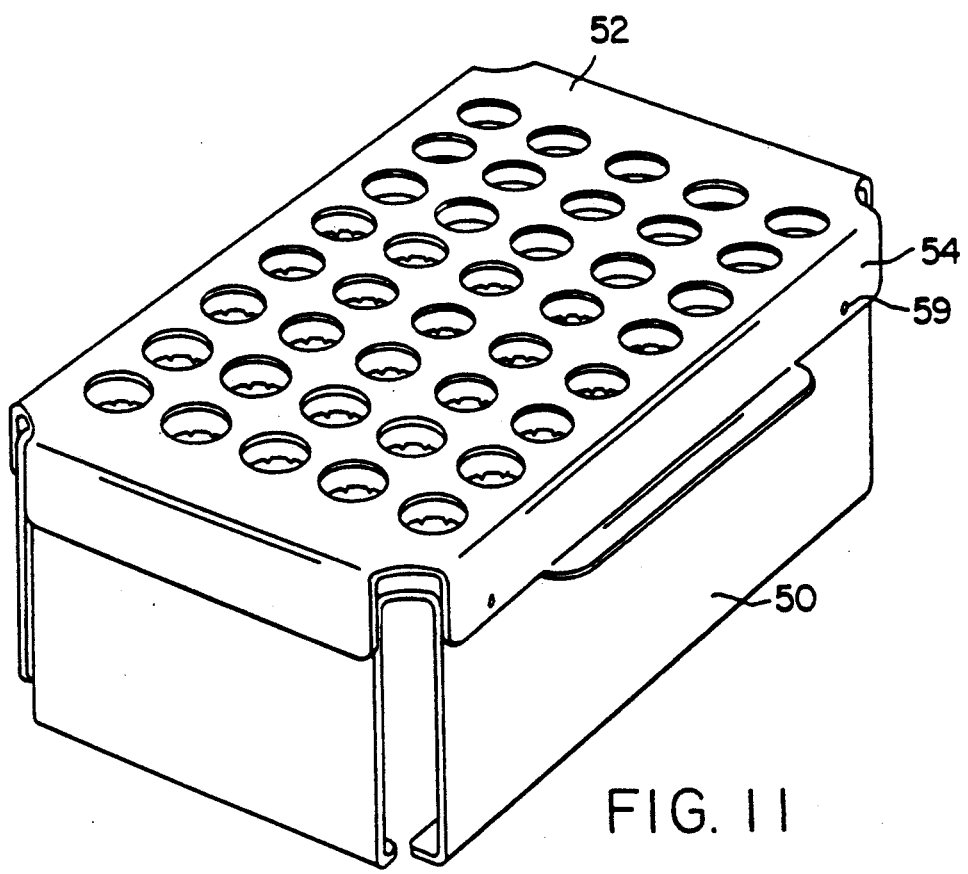
FIG. 11 shows the medical sharp disposal tray system of FIG. 10 which additionally includes a cover.
Figure 12:
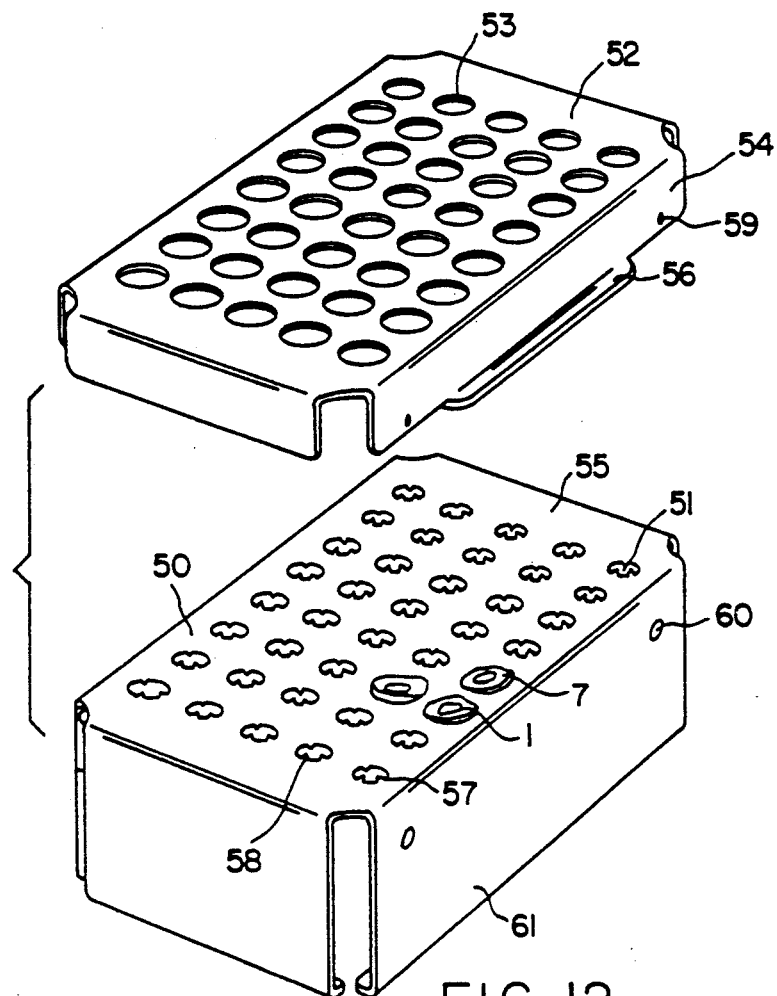
FIG. 12 is an exploded view of the medical sharp disposal tray system of FIG. 11.
Figure 13:
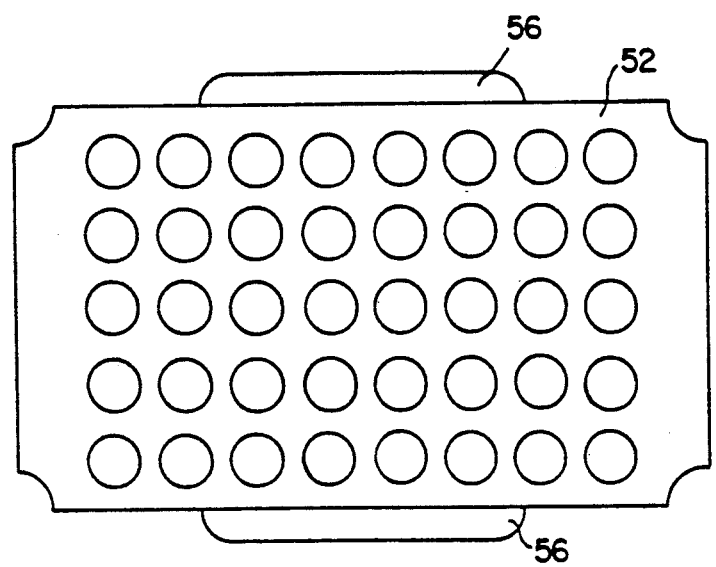
FIG. 13 is a top view of the cover shown in FIGS. 11 and 12.

As shown in FIGS. 11, 12 and 13, a cover 52 may be provided in conjunction with the tray 50. The cover 52 is provided with a plurality of apertures 53, with the arrangement of apertures 53 of the cover 52 corresponding to the arrangement of apertures 51 in the tray 50, although it is not necessary that the size of the apertures 53 correspond to the size of the apertures 51. The cover 52 is placed over the tray 50 containing sheaths 1 in the apertures 51.

If desired, the cover can be provided with alignment means, such as the edge 54 which extends perpendicularly from the top planar surface 53, so that the cover will nest securely over the tray 50. Additionally, the cover can include gripping means, such as the protrusion 56 extending perpendicularly and outwardly from the edge 54. The gripping means assists a user in removing the cover by gripping this gripping means.

The edges 54 of the cover 52, and the tray 60, include interengagement means 59, 60. For example, interengagement means 59 may be holes within edges 54, with interengagement means 60 forming protrusions extending from the outer surface of the sides 60 of the tray 50. The interengagement of the holes and the protrusions holds the cover 52 firmly onto the tray 50 with the flanges 7 of the sheaths between the tray surface and the cover so that even accidental dropping of the tray will not dislodge the cover and thereby cause the sheaths to spill out. Alternatively, each of interengagement means 59, 60 may form corresponding detents. For example, interengagement means 59 may form a protrusion on the inner surface of edge 54 whereas interengagement means 60 forms an indentation in the outer surface of sides 61. Interengagement means 60 may form a protrusion on an outer surface of sides 61, while interengagement means 59 form an indentation in the inner surface of edge 54.

Figure 10:
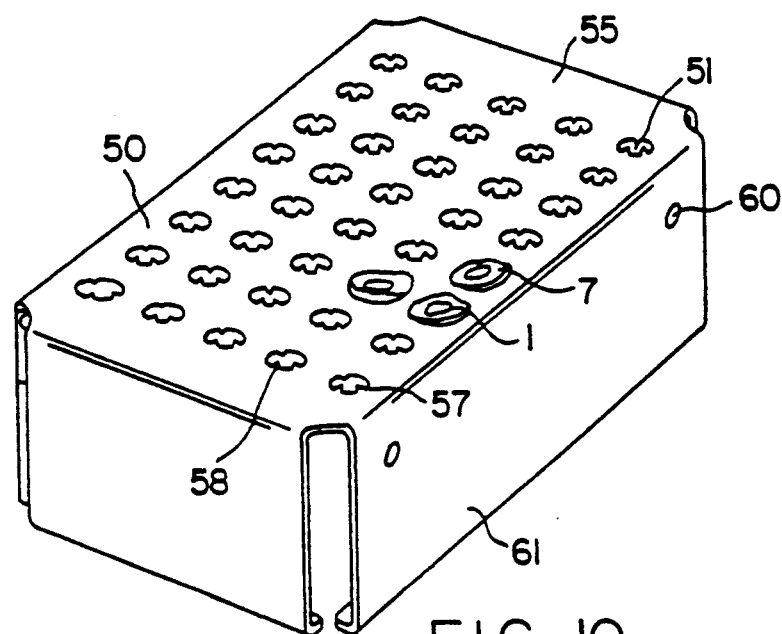
FIG. 10 shows a third embodiment of a medical sharp disposal tray system.

The apertures 51 may be substantially circular to correspond to the diameter of an upper portion of the sheath. Additionally, as illustrated in FIGS. 10 and 12, in a preferred embodiment the apertures 51 are substantially circular and may include means for preventing the rotation of a sheath within the aperture. As shown in FIGS. 10 and 12, the means for preventing rotation for each aperture 51 comprises a plurality of teeth 58 extending radially inward from the circumference of a circular aperture. (Although for illustrative purposes FIGS. 10 and 12 show only several of the apertures 51 as including teeth 58, it is preferred that all the apertures include these teeth.) The teeth 58 engage the vertical ridges 8 (see FIG. 1) underneath the flange 7 of the sheath 1, thereby preventing the sheath from rotating in the aperture 51 during removal of a needle from a syringe. Thus, a needle can be removed from a syringe with only one hand by a user by simply rotating the syringe, after the boss portion is secured within the sheath, with the teeth 58 preventing rotation of the sheath and the needle section secured within.

In operation of this embodiment when the cover is employed, a user places a number of sheaths into the apertures 51 of the tray 50. Subsequently, the cover is placed on the tray, and the interengagement means 59 and 60 are interengaged to firmly hold down the cover onto the tray, as shown in FIG. 11. A user can now insert medical sharps into the sheaths, with the cover providing an additional securing of the sheaths during insertion of the sharp into the sheath. Thus, only a one-handed operation is necessary for the insertion of a needle into a sheath. The cover further serves to help prevent sheaths from falling from the tray.

In a preferred method of using the apparatus, the tray, with the cover removed, is filled with a desired number of sheaths. Subsequently, the cover is placed on the tray which contains sheaths, and a user can now safely disengage the boss portion of a medical sharp engaged within a sheath. When the user is ready to empty the tray of sheaths with sharps engaged therein, the cover is removed, and the sheaths can be disposed of by simply inverting the tray and dumping the sheaths out of the tray and into a disposal container.

The cover and tray in this embodiment may be constructed of any suitable material, as in the previous embodiments, with stainless steel or plastic being preferred, and stainless steel being more preferred. Further, it is apparent that the tray may be constructed of any desired size, with any desired number of apertures. For example, if the tray assembly is to be transported between different locations by a user, such as from room to room in a hospital or a medical lab, the apparatus would be small and light enough to be conveniently carried by a user.

FIGS. 14-19 illustrate procedure trays for use in conjunction with the sheaths. The procedure trays can be used for specific medical procedures within medical facilities, such as for injection, vaccinations, or blood collections at a hospital bedside. This embodiment allows a user to transport or dispose of medical equipment in addition to sharps, such as unused syringes, cannulas, vaccines, injectable solutions, blood collection bottles, etc. Further, the procedure tray helps to ensure that medical sharps can be conveniently disposed of at the location where they have been used rather than being transported to a different location with the sharp section exposed.

As shown in FIGS. 14-19, the medical procedure tray 70 comprises a body having a base 71 and two planar upper surfaces, lower front surface 72 and upper rear surface 73. Lower front surface 72 includes a recess 74 into which medical apparatus, such as unused syringes, may be placed. Upper rear surface 73 comprises a plurality of apertures 75 for receiving the tubular portion 2 and the lower head portion 17 of sheath 1. The flange 7 prevents the sheath from falling through the aperture. As in the above embodiments, a medical sharp can be inserted into a sheath held in an aperture 75 via a one-handed operation.

Figure 14:
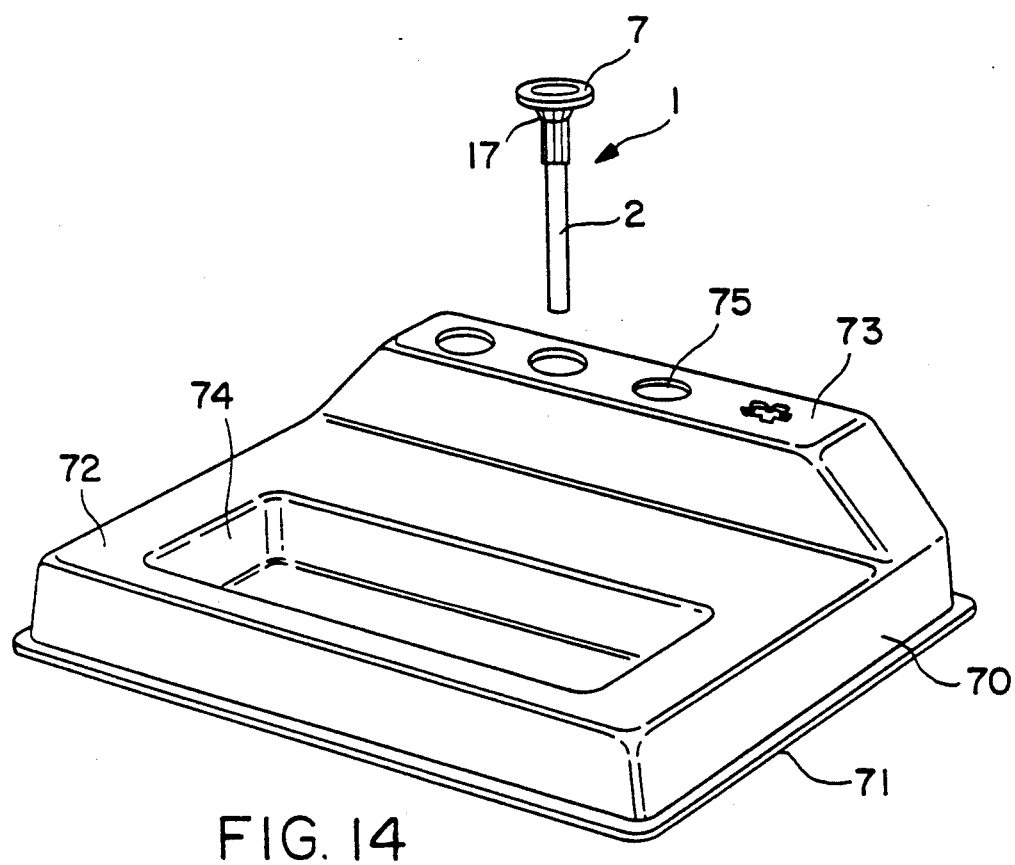
FIG. 14 shows a fourth embodiment of a sharp disposal tray system which serves as a procedure tray.
Figure 15:
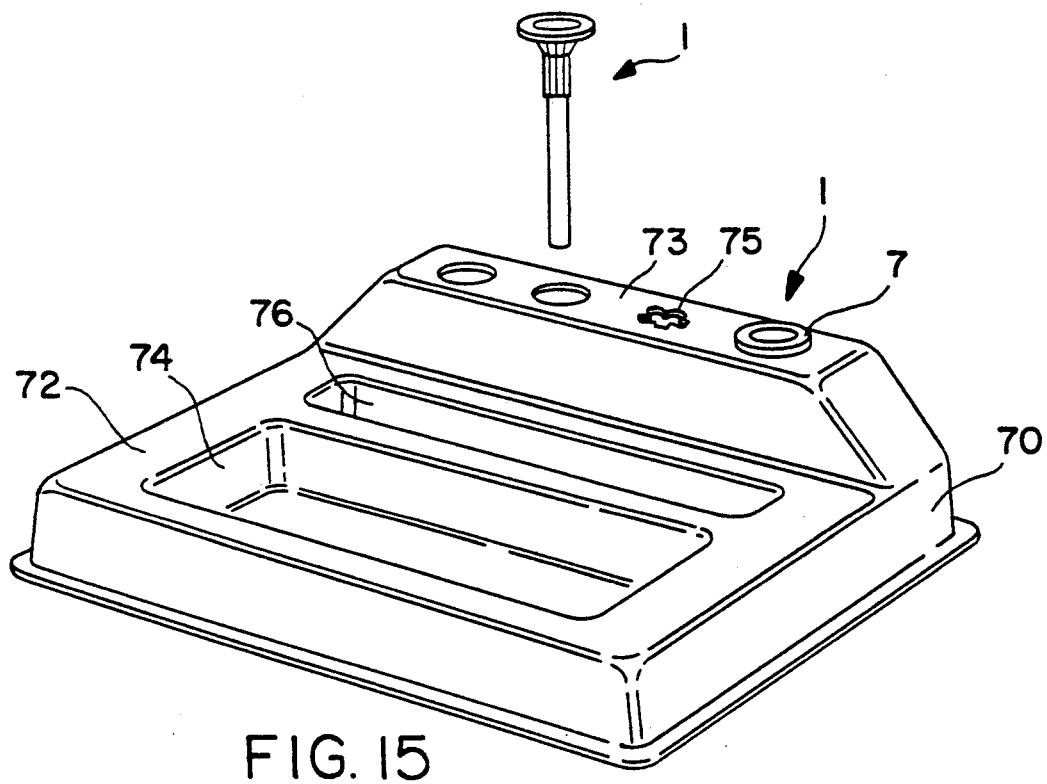
FIGS. 15-18 show alternate embodiments of the procedure tray of FIG. 14.
Figure 16:
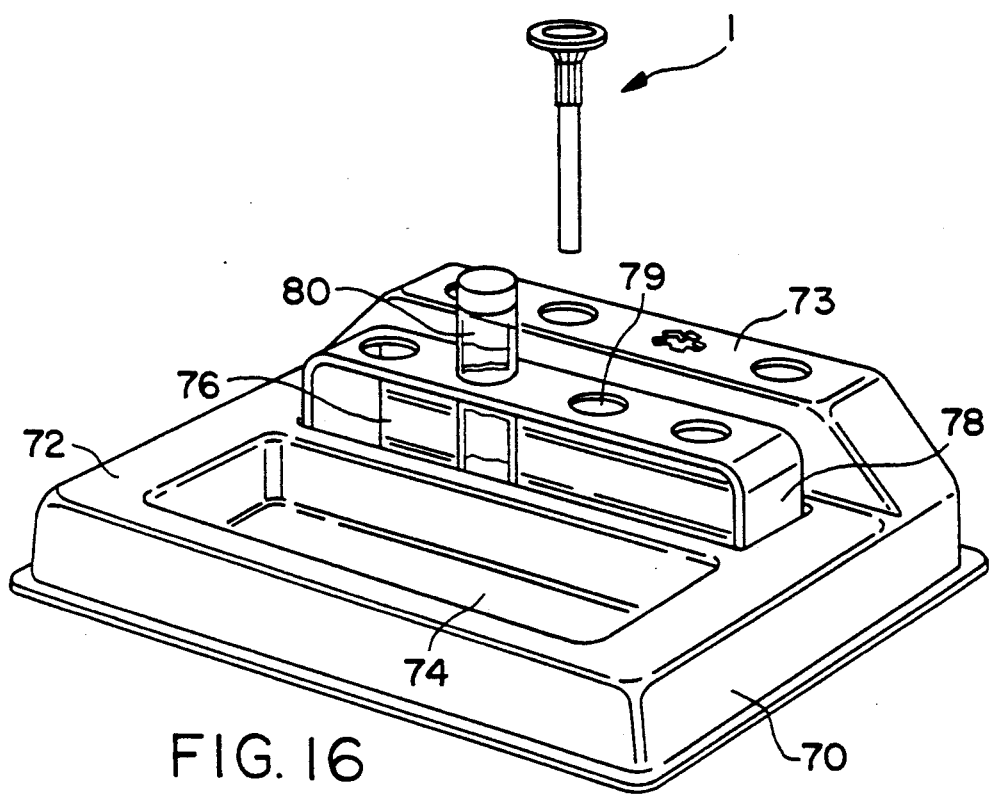

As shown in FIG. 14, lower front surface 72 has only one recess 74. As illustrated in FIG. 15, lower front surface 72 may also include a rear recess 76. In this embodiment one of the recesses may hold unused medical equipment, whereas the other recess would hold used medical equipment. As shown in FIG. 16, the rear recess 76 can hold a rack 78 which comprises at least one aperture 79 for supporting vials 80, such as injection solution vials or sample collection tubes. In this embodiment, the vials 80 are safely supported during use.

Figure 17:
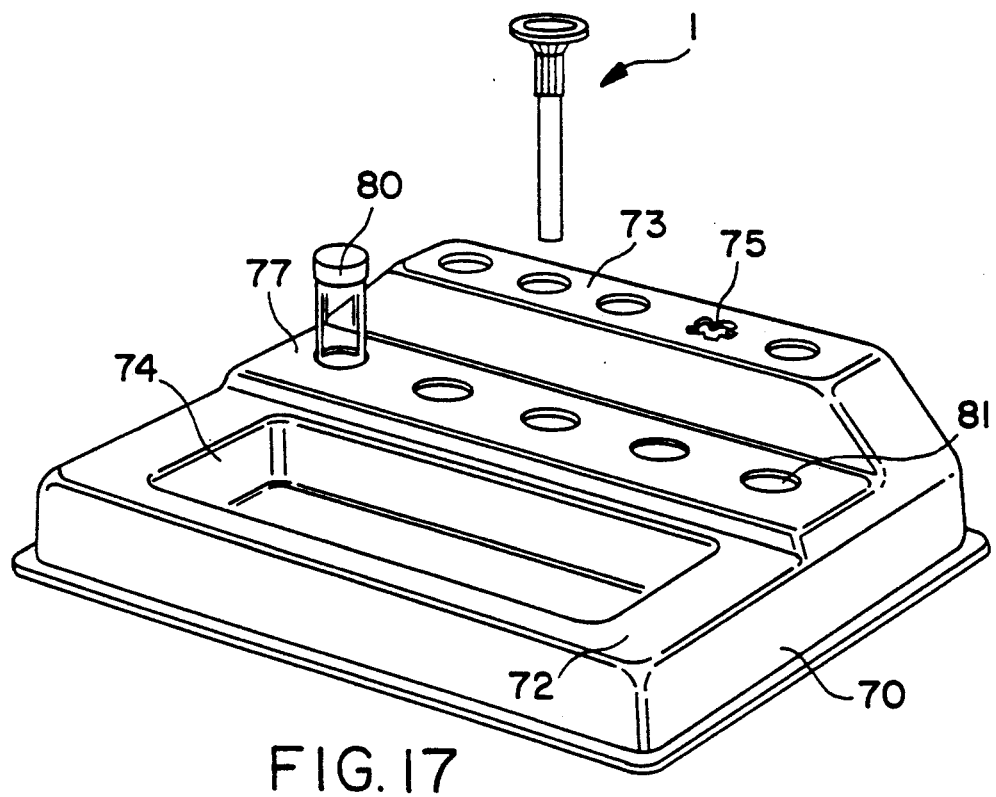

FIG. 17 shows a further embodiment of a procedure tray wherein the procedure tray 70 comprises an intermediate planar portion 77. Intermediate planar portion 77 comprises at least one aperture 81 for supporting vials 80. Additionally, molded recesses (not shown) for supporting vials 80 may extend downward from apertures 81.

Figure 18:
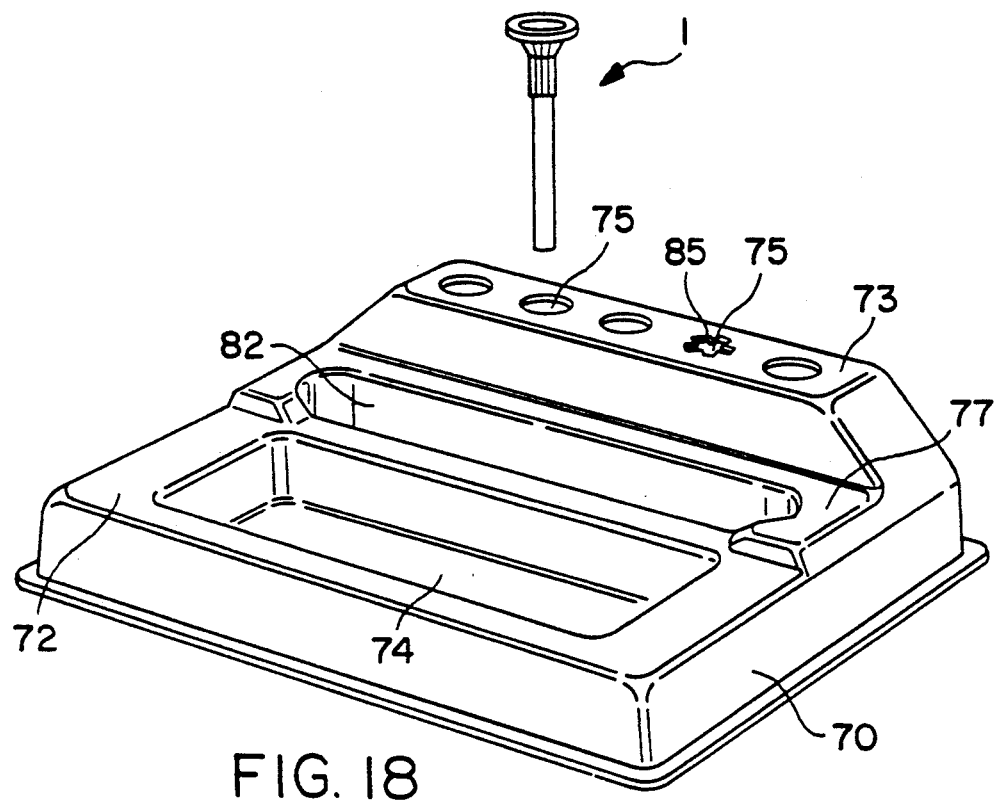
Figure 19:
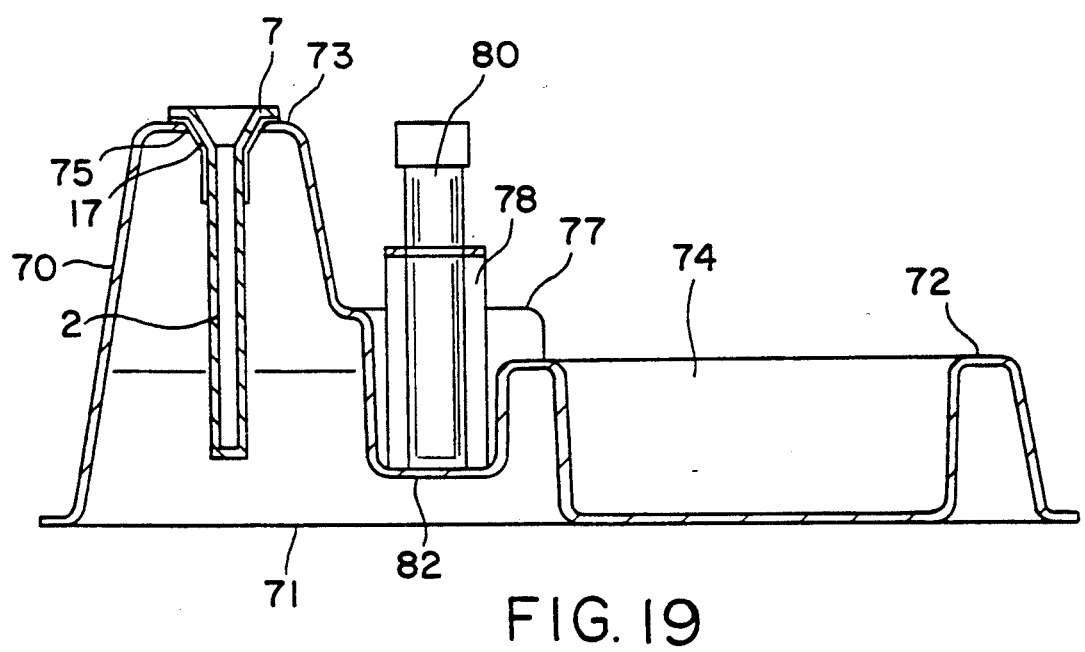
FIG. 19 is a cross-sectional view of the embodiment of FIG. 18 additionally including a rack for supporting sample collection tubes.

FIG. 18 shows the embodiment where intermediate planar portion 77 comprises an elongated recess 82 which can be used either to hold medical equipment or a rack. FIG. 19 is a cross-sectional view of a procedure tray similar to that shown in FIG. 18. Additionally, FIG. 19 illustrates a rack 78 supported in elongated recess 82. As shown in FIG. 19, the sheath is supported in aperture 75 such that the tubular portion 2 does not extend fully to base 71 of the procedure tray.

The apertures 75 may include teeth 85 for preventing the rotation of a sheath, as in the above embodiments, as shown in FIG. 18. Of course, all the apertures may include means for preventing the rotation of a sheath.

As in the other embodiments, the procedure trays may be manufactured from plastic or stainless steel. Preferably, the material is suitable for autoclaving so that the trays may be reused.

What is claimed is:

1. An apparatus for supporting a plurality of sheaths for receiving and holding medical sharps, each sheath comprising a tubular portion closed at a lower end and open at an upper end, said apparatus comprising:
   holding means comprising a planar surface with a plurality of apertures therein, each aperture for receiving and supporting one of said sheaths toward an upper end of the sheath, wherein at least one of said apertures comprises means for preventing the rotation of a sheath;
   said sheaths comprising radial ribs extending longitudinally along the outer surface of the sheath from a point near the open upper end for engagement with said means for preventing the rotation; and
   an upper inner surface of said sheaths comprises means for grippingly engaging a boss portion of a medical sharp, said means for grippingly engaging comprising a plurality of ridges extending radially inward form the inner surface of the tubular portion.

2. The apparatus of claim 1, wherein said planar surface of the holding means is substantially horizontal and the sheaths are held in an upright position in said holding means.

3. The apparatus of claim 1, wherein said means for preventing the rotation of a sheath comprises teeth extending radially inwardly from an inner perimeter of said at least one aperture.

4. The apparatus of claim 3, wherein said at least one aperture is substantially circular, and said teeth extend radially inwardly from the circumference of said at least one aperture.

5. The apparatus of claim 4, wherein each of said apertures are substantially circular and comprise said teeth.

6. The apparatus of claim 1, further comprising a plurality of said sheaths.

7. The apparatus of claim 6, wherein the open upper end of said sheaths includes means for assisting in guiding a tip of a medical sharp into the sheath.

8. The apparatus of claim 7, wherein said means for assisting in guiding the tip of the medical sharp into the sheath comprises a bevelled surface at the upper end of the sheath.

9. The apparatus of claim 1, wherein said means for grippingly engaging comprises an inside portion of the tubular portion being substantially cylindrical and having a diameter to engage with an interference fit the boss of a medical sharp.

10. The apparatus of claim 1, wherein each of the apertures receive and support one of said sheaths toward an upper end thereof securely enough that the medical sharp can be inserted into the sheath by a user of the apparatus with only one hand.

11. An apparatus for supporting a plurality of sheaths for receiving and holding medical sharps, each sheath comprising a tubular portion closed at a lower end and open at an upper end, said apparatus comprising:
   a bottom base;
   a first substantially horizontal planar surface above said bottom base with a plurality of apertures therein, each aperture for receiving and substantially vertically supporting one of said sheaths toward an upper end of the sheath such that the sheaths supported in said apertures do not extend fully to said bottom base; and
   a second substantially horizontal planar surface above said bottom base comprising means for holding medical instruments or supplies, said means for holding forming a first recess within said second planar surface.

12. The apparatus of claim 11, wherein said first planar surface is higher than said second planar surface.

13. The apparatus of claim 11, wherein said means for holding medical instruments or supplies additionally comprises a second recess within said second planar surface, wherein said second recess is of a different size than said first recess.

14. The apparatus of claim 13, additionally comprising a rack having a plurality of apertures therein, each of said rack apertures for supporting medical vials, wherein said rack is removably received in said second recess.

15. The apparatus of claim 12, further comprising a third substantially horizontal planar surface, said third planar surface being higher than said second planar surface and lower than said first planar surface.

16. The apparatus of claim 15, wherein said third planar surface comprises a plurality of apertures, each of said apertures in the third planar surface for supporting a medical vial.

17. The apparatus of claim 15, wherein said third planar surface comprises an additional means for holding medical instruments or supplies, said additional means for holding forming a recess within said third planar surface, wherein said additional recess is of a different size than said first recess.

18. The apparatus of claim 17, additionally comprising a rack having a plurality of apertures therein, each of said rack apertures for supporting medical vials, wherein said rack is removably received in said additional recess.

19. The apparatus of claim 11, wherein the apertures in the holding means include means for preventing the rotation of a sheath.

20. The apparatus of claim 19, wherein each aperture in the holding means is substantially circular, and the means for preventing rotation comprises a plurality of teeth extending radially inwardly from the circumference of the aperture.

21. The apparatus of claim 11, further comprising a plurality of said sheaths.

22. The apparatus of claim 21, wherein the open upper end of said sheaths includes means for assisting in guiding a tip of a medical sharp into the sheath.

23. The apparatus of claim 22, wherein said means for assisting in guiding the tip of the medical sharp into the sheath comprises a bevelled surface at the upper end of the sheath.

24. The apparatus of claim 21, wherein an upper inner surface of said sheaths comprises means for grippingly engaging a boss portion of a medical sharp.

25. The apparatus of claim 24, wherein said means for grippingly engaging comprises a plurality of ridges extending radially inward from the inner surface of the tubular portion.

26. The apparatus of claim 24, wherein said means for grippingly engaging comprises an inside portion of the tubular portion being substantially cylindrical and having a diameter to engage with an interference fit the boss of a medical sharp.

27. The apparatus of claim 11, wherein each of the apertures receive and support one of said sheaths toward an upper end thereof securely enough that the medical sharp can be inserted in the sheath by a user of the apparatus with only one hand.

28. An apparatus for supporting a plurality of sheaths for receiving and holding medical sharps, each of said sheaths comprising a tubular portion closed at a lower end and open at an upper end, the upper inner surface of each of said sheaths comprising means for grippingly engaging a boss portion of said medical sharp, and each of said sheaths further comprising a radial flange around the upper open end of the tubular portion, said apparatus comprising holding means comprising a planar surface with a plurality of apertures therein, each of said apertures for receiving one of said sheaths such that an undersurface of said radial flange is supported on edges of said apertures securely enough that the medical sharp can be inserted into the sheath by a user of the apparatus with only one hand.

29. The apparatus of claim 28, further comprising a plurality of said sheaths.

30. A method for the securing of medical sharps which employs an apparatus comprising sheaths, wherein each sheath comprises a tubular portion closed at a lower end and open at an upper end, and holding means comprising a planar surface with apertures therein, each aperture for receiving and supporting one of said sheaths, said method comprising:
    (a) supporting a desired number of sheaths in said apertures in a substantially upright position and toward the upper end of the sheaths;
    (b) downwardly inserting a sharp section of a medical tool into the tubular portion of one sheath supported in one of said apertures by a user with only one hand while keeping the other hand safely away from the sheath;
    (c) engaging a boss portion of the sharp section located near an upper portion of the sharp section into an upper inner surface of the sheath so that the entire sharp section of the first medical tool is secured within the sheath;
    (d) upwardly lifting the medical tool with the sharp section attached thereto and secured within the sheath to remove the sheath from the aperture; and
    (e) removing the sharp section from an upper section of the medical tool with the sharp section secured within the sheath.

31. The method of claim 30, wherein in step (e), the sharp section is removed for the upper section of the medical tool by twisting the sheath in relation to the upper section of the medical tool with the sharp section remaining secured within the sheath.

32. The method of claim 30, further comprising:
    (f) disposing of the sheath with the sharp section secured therein.

33. The method of claim 32, further comprising repeating steps (b) through (f).

34. A method for the securing of medical sharps which employs an apparatus comprising sheaths, wherein each sheath comprises a tubular portion closed at a lower end and open at an upper end, and holding means comprising a planar surface with apertures therein, each aperture for receiving and supporting one of said sheaths, wherein the apertures comprise means for preventing the rotation of a sheath supported therein, said method comprising:
    (a) supporting a desired number of sheaths in said apertures in a substantially upright position and toward the upper end of the sheaths;
    (b) downwardly inserting a sharp section of a medical tool into the tubular portion of one sheath supported in one of said apertures by a user with only one hand while keeping the other hand safely away from the sheath;
    (c) engaging a boss portion of the sharp section located near an upper portion of the sharp section into an upper inner surface of the sheath so that the entire sharp section of the first medical tool is secured within the sheath;
    (d) rotating an upper section of the medical tool while said means for preventing prevents the rotation of the sheath, thereby removing the upper section of the medical tool from the sharp section with the sharp section remaining secured within the sheath and the sheath remaining within the aperture.

35. The method of claim 34, further comprising repeating steps (b) through (d).

36. The method of claim 30, wherein in step (a), each sheath is supported on an edge of the aperture by ends of radial ribs extending longitudinally along the outer surface of the first sheath from a point near the open upper end.

37. The method of claim 30, wherein in step (a), each sheath is supported on an edge of the aperture by an undersurface of a radial flange around the open upper end of the first sheath.

38. The method of claim 30, wherein step (a) comprises supporting a plurality of said sheaths in the apertures.

39. The method of claim 30, wherein step (a) further comprises engaging a cover over the planar surface of the holding means after a desired number of sheaths are supported in the apertures of the holding means, said cover comprising a planar surface with apertures therein, said apertures in the cover means arranged to substantially correspond to an arrangement of the apertures in the holding means.

40. A method for the securing of medical sharps which employs an aperture comprising sheaths and a planar surface with apertures therein, wherein each sheath comprises a tubular portion and is attached to an integral with said planar surface such that the tubular portion extends perpendicularly downward form one of said apertures, said method comprising:
  (a) downwardly inserting a sharp section of a medical tool to the tubular portion of one sheath by a user with only one hand while keeping the other hand safely away form the sheath;
  (b) engaging a boss portion of the sharp section located near an upper portion of the sharp section into an upper inner surface of the tubular portion of the sheath so that the entire sharp section of the medical tool is secured within the sheath; and p1
  (c) removing the sharp section from an upper section of the medical tool with the sharp section remaining secured within the sheath.

41. The method of claim 40, wherein in step (c), the sharp section is removed from the upper section of the medical tool by twisting the upper section with the sharp section secured within the sheath.

42. The method of claim 69, further comprising disposing of said apparatus after a desired number of the sheaths have sharp sections secured therein.

43. The method of claim 34, wherein in step (a), each sheath is supported on an edge of the aperture by ends of radial ribs extending longitudinally along the outer surface of the first sheath for a point near the open upper end.

44. The method of claim 34, wherein in step (a), each sheath is supported on an edge of the aperture by a undersurface of a radial flange around the open upper end of the first sheath.

45. The method of claim 34, wherein step (a) comprises supporting a plurality of said sheaths in the apertures.

46. The method of claim 34, wherein in step (a), further comprises engaging a cover over the planar surface of the holding means after a desired number of sheaths are supported in the apertures of the holding means, said cover comprising a planar surface with apertures therein, said apertures in the cover means arranged to substantially correspond to an arrangement of the apertures in the holding means.

* * * * *